United States Patent [19]
Gerlitz et al.

[11] Patent Number: 5,596,065
[45] Date of Patent: Jan. 21, 1997

[54] WATER-DILUTABLE URETHANE RESINS, PROCESS FOR THE PREPARATION, AND THE USE THEREOF

[75] Inventors: Martin Gerlitz; Rami-Raimund Awad; Thomas Fraydl, all of Graz, Austria

[73] Assignee: Vianova Resins AG, Graz, Austria

[21] Appl. No.: 506,761

[22] Filed: Jul. 26, 1995

[30] Foreign Application Priority Data

Jul. 27, 1994 [AT] Austria .................. A-1481/94

[51] Int. Cl.⁶ .................................................. C08G 18/10
[52] U.S. Cl. .................. 528/71; 524/591; 524/840; 528/49; 528/75; 528/67

[58] Field of Search .................. 528/49, 71, 75; 524/591, 840

[56] References Cited

U.S. PATENT DOCUMENTS 5,247,048  9/1993  Meixner et al. .................. 528/67
5,300,615  4/1994  Meixner et al. .................. 528/67

*Primary Examiner*—Morton Foelak
*Attorney, Agent, or Firm*—Foley & Lardner

[57] ABSTRACT

Process for the preparation of water-dilutable urethane resins and use of the so produced urethane resins, for example, as binders for coating materials which can be crosslinked by free-radical polymerization.

20 Claims, No Drawings

WATER-DILUTABLE URETHANE RESINS, PROCESS FOR THE PREPARATION, AND THE USE THEREOF

BACKGROUND OF THE INVENTION

1. Field of the Invention

The invention relates to water-dilutable urethane resins, processes for the preparation thereof, and to their use, for example, as binders for coating materials which can be crosslinked by free-radical polymerization.

2. Description of Related Art

Water-soluble or dispersible polyurethanes which contain carboxyl groups in the form of structural units of dimethylolpropionic acid and which are suitable as coating materials for substrates are known, for example, from EP 0 269 972 A2.

The preparation of similarly structured oligourethanes, which can be cured by free-radical polymerization, is described in EP 0 453 838 A2. Here, a mixture of alcohols containing (meth)acryloyl groups and dimethylolpropionic acid is reacted with diisocyanates in the presence of an organic solvent, such as butyl acetate, and the reaction product is converted by means of ammonia into the water-dilutable form.

Oligourethanes of this kind have significant disadvantages. For example, prior to dispersion in water, the products are from 60 to 95% strength solutions in organic solvents. Only part of the organic solvent can be removed, since the viscosity of the resins increases rapidly as the solids content rises. Moreover, the use of ammonia as a neutralizing agent for water-dilutable coating materials is being rejected more and more all the time.

SUMMARY OF THE INVENTION

Accordingly, it is an object of the present invention to provide urethane resins and processes for their preparation and use, which overcomes drawbacks of the urethane resins of the prior art. It has now been found that, by making a specific choice of raw materials and, in particular, by specific process steps, it is possible to prepare water-dilutable urethane resins which, in the form in which they are used, are free from monomers and organic solvents and can be cured without emissions.

In accordance with the invention, there is provided a process for the preparation of water-dilutable urethane resins comprising reacting (A) hexamethylene diisocyanate, a total of 50 mol % of whose NCO groups are in the form of urethane groups due to reaction of the hexamethylene diisocyanate with (i) one or more alcohols containing (meth)acryloyl groups and optionally with (ii) one or more aliphatic monoalcohols, with (B) from 0.25 to 0.45 mol per mol of (A) of 2,2-bis(hydroxymethyl)propionic acid at from 70° to 90° C. until complete reaction of the hydroxyl groups has taken place, to obtain intermediate (AB) groups, and then reacting the intermediate (AB) with (C) from 0.2 to 0.45 mol per mol of (A) of one or more of an aliphatic or cycloaliphatic diisocyanate, a total of 50 mol% of whose NCO groups are in the form of urethane groups due to reaction with (i) one or more alcohols containing (meth)acryloyl groups and optionally with (ii) one or more aliphatic monoalcohols, at from 100° to 110° C. until complete reaction of the remaining free isocyanate groups to give allophanate groups has taken place thereby giving a reaction product (ABC), wherein the molar ratios of components (A), (B), and (C) is such that the ratio of equivalents of the isocyanate groups and hydroxyl groups present in the original raw materials for component (A), (B), and (C) is from 1.1:1 to 1.45:1; and wherein the reaction product (ABC) contains carboxyl groups corresponding to an acid number of from 25 to 50 mg of KOH/g, and wherein at least 45% of the carboxyl groups of (ABC) are then neutralized with (D) an alkali metal hydroxide, optionally as a mixture with (E) an aliphatic or cycloaliphatic diisocyanate whose NCO groups are reacted to the extent of 50 mol % each with one or more alcohols containing (meth)acryloyl groups and the remaining NCO groups are reacted with one or more N,N-dialkylalkanolamines, to form urethane groups, wherein the end product has a double bond equivalent (number of moles of ethylenic double bond per 1000 g of resin as solid) of from 1.5 to 3.5 mmol/g.

In accordance with other objects of the invention, there is provided urethane resins produced by this process and methods of using the urethane resins prepared in accordance with the invention as binders for water-dilutable coating materials, which can be crosslinked by free-radical polymerization.

Further objects, features, and advantages will become apparent from the detailed description of preferred embodiments that follows.

DETAILED DESCRIPTION OF PREFERRED EMBODIMENTS

The urethane resins of the present invention can be employed free from monomers and organic solvents, can be cured without emissions, and as a coated film, show a high degree of crosslinking.

Component (A) comprises hexamethylene diisocyanate, a total of 50 mol % of whose NCO groups are in the form of urethane groups after the reaction with alcohols containing (meth)acryloyl groups and, if desired, with aliphatic monoalcohols.

The alcohols containing (meth)acryloyl groups may be any known and generally are esters, containing one or two free hydroxyl group(s), of (meth)acrylic acid with dihydric to tetrahydric alcohols and/or with mono- or diglycidyl compounds.

The aliphatic monoalcohols which are used if desired in component (A) for the urethanization of NCO groups, may be any known and generally contain alkyl radicals having from six to fourteen carbon atoms. The proportion of these monoalcohols, based on the overall quantity of hydroxyl groups which are available for the conversion of the isocyanate groups, is preferably not more than 40 mol %.

As component (B), 2,2-bis(hydroxymethyl)propionic acid (dimethylolpropionic acid, DMPA) is employed.

Component (C) largely corresponds in its composition to component (A). In contrast to component (A), the raw materials used in component (C), however, may also comprise, in addition to, the preferred hexamethylene diisocyanate, another aliphatic diisocyanate and/or a cycloaliphatic diisocyanate, preferably isophorone diisocyanate. The alcohols containing (meth) acryloyl groups should preferably only contain one single free hydroxyl group.

Components (A) and (C) are prepared in any known manner, for example, the diisocyanates are introduced as initial charge and the alcohols are added over the course of from 30 minutes to 3 hours, taking into account the exothermic reaction which takes place, at a rate such that the reaction temperature does not exceed from 40° to 50° C. The reaction mixture is stirred until the theoretical NCO content has been reached.

Only when the reaction of the diisocyanates to the corresponding "monourethanes" is as quantitative as possible, are the required low molecular weight intermediates, which are therefore of sufficiently low viscosity, obtained. Thus, in components (A) and (C) about 50 mol % of the NCO groups are urethanized.

As component (D), any desired hydroxide can be used. In addition to NaOH or KOH, it is preferred to use lithium hydroxide.

Component (E) comprises an aliphatic or cycloaliphatic diisocyanate whose isocyanate groups, due to reaction to the extent of 50 mol % each with alcohols containing (meth-)acryloyl groups and the remaining NCO groups are reacted with N,N-dialkylalkanolamines, such as dimethyl- or diethylethanolamine, are in the form of urethane groups.

In order to prepare component (E), a component prepared as in (C) (but generally not obtained with the optional aliphatic monoalcohols used in (C)) is reacted with equimolar quantities of the dialkylalkanolamine, in the course of which reaction the temperature should not exceed a maximum of 50° C. The reaction mixture is stirred until no free NCO groups can be detected.

In order to carry out the process according to the invention, per 1.0 mol of component (A), is reacted from 0.25 to 0.45 mol of 2,2-bis(hydroxy methyl)propionic acid (component B) at from 70° to 90° C. until complete reaction of the hydroxyl groups has taken place. The intermediate (AB) thus obtained is subsequently reacted with from 0.2 to 0.45 mol of component (C) at from 100° to 110° C. until complete reaction of the remaining free isocyanate groups to give allophanate groups has taken place. The molar ratios of components (A), (B), and (C) combined are chosen such that the ratio of equivalents of the isocyanate groups and hydroxyl groups present originally in the raw materials for components (A), (B) and (C) is from 1.1:1 to 1.45:1.

Corresponding to an acid number of from 25 to 50 mg of KOH/g, the reaction product contains carboxyl groups which are neutralized to the extent of at least 45% with component (D), if desired in a mixture with component (E), the proportion of which may be up to 50 equivalent %.

The end product generally has a double bond equivalent (number of moles of ethylenic double bonds per 1000 g of resin as solids) of from 1.5 to 3.5 mmol/g.

The usual catalysts, for example as shown in the following examples, can be used in preparing the urethane resins.

The selection of specific raw materials and the synthesis route adopted therefore make it possible to prepare low-viscosity urethane resins. They are especially useful wherever urethane resin can be used. They are useful as binders for coating materials which can be crosslinked by free-radical polymerization, especially by means of UV irradiation, and which in the form in which they are used are free from monomers and organic solvents, can be cured without emissions and, as coating films, show a high degree of crosslinking.

The formulations of the coating materials for the desired various applications, and the production and processing of such coating materials, are known to those skilled in the art and can be taken from the technical literature.

The following examples illustrate the invention without limiting it in its scope. All parts or percentages relate, unless stated otherwise, refer to units by weight.

In the examples, the following abbreviations for raw materials are used:
a) Diisocyanates:
  HDI Hexamethylene diisocyanate
  IPDI Isophorone diisocyanate
b) Alcohols containing (meth)acryloyl groups:
  ALK 1 2-hydroxy-1-acryloyloxy-3-methacryloyoxypropane (reaction product of glycidyl methacrylate with acrylic acid)
  ALK 2 Polypropylene glycol monoacrylate (Bisomer PPA6E; from INSPEC, GB)
  ALK 3 Hexanediol diglycidyl ether diacrylate
  ALK 4 Hydroxyethyl acrylate
  ALK 5 Hydroxypropyl acrylate
  ALK 6 Reaction product of TMP-3EO (Polyol TP 300, from PERSTORP, SE) with 2 mol of acrylic acid, MW 373, OH number: 150 mg of KOH/g;
  ALK 7 Pentaerythritol triacrylate
c) Aliphatic monoalcohols:
  ALK 8 2-ethylhexanol
  ALK 9 isononyl alcohol
d) DMPA Dimethylolpropionic acid
e) N,N-dialkylalkanolamines:
  DMEA N,N-dimethylethanolamine
  DEEA N,N-diethylethanolamine
f) Catalysts:
  TEA Triethylamine
  DBTL Dibutyltin dilaurate
g) Polymerization inhibitors:
  HMME Hydroquinone monomethyl ether
  HQ Hydroquinone
  BHT Butylated hydroxytoluene 1. Preparation of components (A1) to (A4)

In accordance with the information in Table 1, 1.0 mol of HDI is reacted in the presence of a suitable catalyst (DBTL) by dropwise addition of 1.0 mol of alcohol for from 30 minutes to 3 hours at not more than 40° C. to give the corresponding monourethane. The reaction temperature is a function of the nature and quality of the alcohols used (primary or secondary hydroxyl groups, impurities) and is determined in preliminary experiments for the individual starting materials. The reaction mixture is maintained at the corresponding temperature until the theoretical NCO content has been reached.

2. Preparation of components (C1) to (C5)

Analogous to section 1; the reaction temperature for IPDI is not more than 55° C.

3. Preparation of components (E1) to (E3)

In accordance with the information in Table 2, products selected among components (A) and (C) are reacted with an N,N-dialkylalkanolamine, after addition of a polymerization inhibitor (HQ, HMME), at not more than 50° C. in a highly exothermic reaction until no free NCO groups can be detected, with the N,N-dialkylalkanolamine being introduced as initial charge and air being passed into the reaction mixture.

TABLE 1

| | Parts (mol) of diisocyanate | | | Parts (mol) of alcohol | | | Reaction temperature | MW | NCO content in % by wt. | DBE (mmol/g) |
|---|---|---|---|---|---|---|---|---|---|---|
| (A1) | 168 | (1.0) | HDI | 183 | (0.85) | ALK 1 | 30–40° C. | 372.6 | 11.2 | 4.56 |
| | | | | 21.6 | (0.15) | ALK 9 | | | | |
| (A2) | 168 | (1.0) | HDI | 47 | (0.2) | ALK 3 | 30–40° C. | 319 | 13.1 | 3.13 |
| | | | | 104 | (0.8) | ALK 5 | | | | |
| (A3) | 168 | (1.0) | HDI | 252 | (0.6) | ALK 2 | 30–40° C. | 539 | 7.7 | 3.34 |
| | | | | 119 | (0.4) | ALK 7 | | | | |
| (A4) | 168 | (1.0) | HDI | 64.5 | (0.3) | ALK 1 | 30–40° C. | 445 | 9.4 | 3.60 |
| | | | | 186.5 | (0.5) | ALK 6 | | | | |
| | | | | 26 | (0.2) | ALK 8 | | | | |
| (C1) | 134.4 | (0.8) | HDI | 168 | (0.4) | ALK 2 | 50° C. | 424.8 | 9.8 | 1.41 |
| | 44.4 | (0.2) | 1801 | 26 | (0.2) | ALK 5 | | | | |
| | | | | 52 | (0.4) | ALK 8 | | | | |
| (C2) | 222 | (1.0) | IPDI | 116 | (1.0) | ALK 4 | 50° C. | 338 | 12.4 | 2.95 |
| (C3) | 168 | (1.0) | HDI | 26 | (0.2) | ALK 5 | 30–40° C. | 305 | 13.7 | 0.66 |
| | | | | 39 | (0.3) | ALK 8 | | | | |
| | | | | 72 | (0.5) | ALK 9 | | | | |
| (C4) | 222 | (1.0) | IPDI | 23.2 | (0.2) | ALK 4 | 50° C. | 349.2 | 12.0 | 0.57 |
| | | | | 104 | (0.8) | ALK 8 | | | | |
| (C5) | 168 | (1.0) | HDI | 130 | (1.0) | ALK 5 | 30–40° C. | 298 | 14.0 | 3.35 |

TABLE 2

| | Parts (mol) of diisocyanate precursor | | | Parts (mol) of alkanolamine | | | Reaction temperature | MW | DBE |
|---|---|---|---|---|---|---|---|---|---|
| (E1) | 298 | (1.0) | (C5) | 89 | (1.0) | DMEA | 50° C. | 387 | 2.58 |
| (E2) | 338 | (1.0) | (C2) | 89 | (1.0) | DMEA | 50° C. | 427 | 2.33 |
| (E3) | 338 | (1.0) | (C2) | 118 | (1.0) | DEEA | 50° C. | 456 | 2.18 |

4. Examples 1 to 4

In accordance with the information in Table 3, a polymerization inhibitor (HQ, HMME, BHT) and DMPA are added to component (A). The reaction mixture is held at 70° C., taking into account the exothermic reaction, and air is passed continually through the mass. If required, the temperature can be increased gradually to 90° C. The end of the reaction is reached at the NCO content which corresponds to complete conversion of all hydroxyl groups.

Following addition of component (C) and, if desired, of a catalyst (DBTL, TEA), the reaction mixture is heated to not more than 110° C. and held at this temperature until no free NCO groups can be detected.

The reaction product is finally neutralized in accordance with the information in Table 3 and diluted with deionized water to the desired solids content.

5. Comparison examples C1 and C2

Products prepared in accordance with the information in EP 0 453 838 A2, hereby incorporated by reference, Examples 5 and 6, respectively, in step c) with a content of as yet unreacted NCO groups of 1% and 2.5%, respectively, were at 100° C. already so viscous that they had to be diluted with butyl acetate.

TABLE 3

| Component | Example 1 Parts (mol) | Example 2 Parts (mol) | Example 3 Parts (mol) | Example 4 Parts (mol) |
|---|---|---|---|---|
| (A1) | 372.6 (1.0) | | | |
| (A2) | | 319 (1.0) | | |
| (A3) | | | 539 (1.0) | |
| (A4) | | | | 445 (1.0) |
| (B) | 60.3 (0.45) | 53.6 (0.40) | 46.9 (0.35) | 37.5 (0.28) |
| (C1) | 127.5 (0.3) | | | |
| (C2) | | 118.3 (0.35) | | |
| (C3) | | | 122 (0.40) | |
| (C4) | | | | 87.3 (0.25) |
| (NCO:OH in equivalents) | 1.18:1 | 1.25:1 | 1.33:1 | 1.38:1 |
| Acid number | 45 | 46 | 28 | 28.5 |
| (D) 3LiOH | 5.19 g | 4.84 g | 5.73 g | 3.48 g |
| (E1) | 20.9 g | | | |
| (E2) | | | 34.0 g | |
| (E3) | | | | 66.1 g |
| Degree of neutralization | 60% | 50% | 90% | 100% |
| D:E in equiv. % | 80:20 | 100:0 | 75:25 | 50:50 |

TABLE 3-continued

| Component | Example 1 Parts (mol) | Example 2 Parts (mol) | Example 3 Parts (mol) | Example 4 Parts (mol) |
|---|---|---|---|---|
| DBE | 3.30 mmol/g | 2.72 mmol/g | 2.62 mmol/g | 2.81 mmol/g |
| Aliphatic alcohols | 12 mol % | 0 mol % | 15 mol % | 22 mol % |

6. Performance testing of the water-dilutable urethane resins prepared in accordance with Examples 1 to 4 as coating materials Water-dilutable, UV-curable white paint

| | |
|---|---|
| 250.0 | Urethane resin, 40% in water, according to Example 1 or 2 |
| 80.0 | TiO$_2$ (rutile) |
| 0.9 | Defoamer, silicone-free |
| 0.4 | Levelling agent, silicone-free |
| 2.0 | Photoinitiator 1 (DAROCUR ® 1173, CIBA-GEIGY) |
| 1.0 | Photoinitiator 2 (LUCIRIN ® TPO, BASF) |
| 30.0 | Water, deionized |
| 364.3 | |

Water-dilutable, UV-curable clearcoat

| | |
|---|---|
| 100.0 | Urethane resin, 40% in water, according to Example 3 or 4 |
| 0.5 | Defoamer, silicone-free |
| 1.0 | Substrate wetting agent |
| 2.0 | Photoinitiator (DAROCUR ® 1173, CIBA-GEIGY) |
| 5.0 | Water, deionized |
| 108.5 | |

The coating materials, prepared in a conventional manner, are adjusted with LiOH, 5% strength in water, to a pH of from 7.9 to 8.3, diluted with deionized water to the required viscosity and applied by spraying to glass or metal panels.
Curing conditions:
Forced air drying for 5 min at 55° C., UV curing with high-pressure mercury lamp (pigmented formulation: gallium-doped high-pressure mercury lamp), 80 watt/cm, distance from object about 10 cm, belt speed 4 m/min.
Test methods and test results:
Pendulum hardness:
In accordance with DIN 53157, glass plates, layer thickness (wet film) 150 μm.
Mechanical deformability (Erichsen indentation):
Tested in accordance with ISO 1520, Bonder metal panel, layer thickness (wet film) 120 μm.
Acetone resistance:
In accordance with DIN 68861, glass plates, layer thickness (wet film) 150 μm.

| | White paint | | Clearcoat | |
|---|---|---|---|---|
| Binder | Example 1 | Example 2 | Example 3 | Example 4 |
| Pendulum hardness [s] | 168 | 156 | 170 | 162 |
| Indentation [mm] | 7.8 | 7.4 | 8.8 | 8.7 |
| Acetone resistance [min] | 150 | 135 | 188 | 200 |

It is intended that the specification be considered as exemplary only. Other embodiments of the invention will be apparent to those skilled in the art from consideration of the specification and practice of the invention disclosed herein.

What is claimed is:

1. A process for the preparation of water-dilutable urethane resins comprising:

reacting (A) hexamethylene diisocyanate, a total of 50 mol % of whose NCO groups are in the form of urethane groups due to reaction of the hexamethylene diisocyanate with (i) one or more alcohols containing (meth)acryloyl groups and optionally with (ii) one or more aliphatic monoalcohols, with (B) from 0.25 to 0.45 mol per mol of (A) of 2,2-bis(hydroxymethyl)propionic acid at from 70° to 90° C. until complete reaction of the hydroxyl groups has taken place, to obtain intermediate (AB), and then reacting the intermediate (AB) with (C) from 0.2 to 0.45 mol per mol of (A) of one or more of an aliphatic or cycloaliphatic diisocyanate, a total of 50 mol % of whose NCO groups are in the form of urethane groups due to reaction with (i) one or more alcohols containing (meth)acryloyl groups and optionally with (ii) one or more aliphatic monoalcohols, at from 100° to 110° C. until complete reaction of the remaining free isocyanate groups to give allophanate groups has taken place thereby giving a reaction product (ABC), wherein the molar ratios of components (A), (B), and (C) is such that the ratio of equivalents of the isocyanate groups and hydroxyl groups present in the original raw materials for components (A), (B), and (C) is from 1.1:1 to 1.45:1; and wherein the reaction product (ABC) contains carboxyl groups corresponding to an acid number of from 25 to 50 mg of KOH/g, and wherein at least 45% of the carboxyl group of (ABC) are then neutralized with (D) an alkali metal hydroxide, optionally as a mixture with (E) an aliphatic or cycloaliphatic diisocyanate whose NCO groups are reacted to the extent of 50 mol % each with one or more alcohols containing (meth)acryloyl groups and with one or more N,N-dialkylalkanolamines, to form urethane groups, wherein the end product has a double bond equivalent (number of moles of ethylenic double bond per 1000 g of resin as solid) of from 1.5 to 3.5 mmol/g.

2. A process according to claim 1, wherein component (C) comprises an aliphatic diisocyanate.

3. A process according to claim 1, wherein component (E) is used.

4. A process according to claim 3, wherein an aliphatic diisocyanate is employed in components (C) and (E) and wherein the aliphatic diisocyanate used in (C) or (E) or both (C) and (E) comprises hexamethylene diisocyanate.

5. A process according to claim 1, wherein component (C) comprises a cycloaliphatic diisocyanate.

6. A process according to claim 3, wherein a cycloaliphatic diisocyanate is employed in components (C) and (E) and wherein the cycloaliphatic diisocyanate used in (C) or (E) or both (C) and (E) comprises isophorone diisocyanate.

7. A process according to claim 1, wherein the alcohols containing (meth)acryloyl groups of component (A) comprise esters, containing one or two free hydroxyl groups, of (meth)acrylic acid with one or more dihydric to tetrahydric alcohols or mono- or diglycidyl compounds.

8. A process according to claim 1, wherein the alcohols containing (meth)acryloyl groups in component (C) comprise esters, containing one single free hydroxyl group, of (meth)acrylic acid with one or more of dihydric to tetrahydric alcohols or mono- or diglycidyl compounds.

9. A process according to claim 3, wherein the alcohols containing (meth)acryloyl groups in component (E) comprise esters, containing one single free hydroxyl group, of (meth)acrylic acid with one or more of dihydric to tetrahydric alcohols or mono- or diglycidyl compounds.

10. A process according to claim 1, wherein the component (A) is formed from aliphatic monoalcohols whose alkyl radicals contain from six to fourteen carbon atoms and wherein the monoalcohols are employed in a proportion of not more than 40 mol %, based on the overall quantity of hydroxyl groups available for urethanization of NCO groups.

11. A process according to claim 3, wherein component (C) is formed from aliphatic monoalcohols whose alkyl radicals contain from six to fourteen carbon atoms and wherein the monoalcohols are employed in a proportion of not more than 40 mol %, based on the overall quantity of hydroxyl groups available for urethanization of NCO groups.

12. A process according to claim 1 wherein component (D) comprises lithium hydroxide.

13. A process according to claim 1, wherein the N,N-dialkylalkanolamine in component (E) is N,N-dimethylethanolamine, N,N-diethylethanolamine, or a mixture thereof.

14. A process according to claim 1, wherein based on a mixture of components (D) and (E), component (E) is employed in a proportion of up to 50 equivalent %.

15. A urethane resin produced by a process according to claim 1.

16. A urethane resin produced by a process according to claim 3.

17. A coating material comprising a urethane resin according to claim 15 as binder.

18. A coating material as claimed in claim 17, which can be crosslinked by free-radical polymerization, which is free from monomers and organic solvents, which can be cured without emissions, and which shows a high degree of crosslinking.

19. A substrate coated with a material as claimed in claim 17.

20. A urethane resin as claimed in claim 15, which is free of organic solvents.

* * * * *